(12) United States Patent
Kameyama et al.

(10) Patent No.: US 9,238,052 B2
(45) Date of Patent: Jan. 19, 2016

(54) METHOD FOR PRODUCING HIPPOCASTANACEAE PLANT SEED EXTRACT

(75) Inventors: Akiyo Kameyama, Haga-gun (JP); Tsutomu Fujimura, Haga-gun (JP)

(73) Assignee: Kao Corporation, Tokyo (JP)

( * ) Notice: Subject to any disclaimer, the term of this patent is extended or adjusted under 35 U.S.C. 154(b) by 423 days.

(21) Appl. No.: 12/867,092

(22) PCT Filed: Feb. 10, 2009

(86) PCT No.: PCT/JP2009/052602
§ 371 (c)(1),
(2), (4) Date: Aug. 11, 2010

(87) PCT Pub. No.: WO2009/102075
PCT Pub. Date: Aug. 20, 2009

(65) Prior Publication Data
US 2010/0310689 A1    Dec. 9, 2010

(30) Foreign Application Priority Data

Feb. 13, 2008  (JP) ................................ 2008-031274
Sep. 5, 2008   (JP) ................................ 2008-228161

(51) Int. Cl.
*A61K 36/77*        (2006.01)

(52) U.S. Cl.
CPC ...................................... *A61K 36/77* (2013.01)

(58) Field of Classification Search
None
See application file for complete search history.

(56) References Cited

U.S. PATENT DOCUMENTS 2,512,107 A * 6/1950 Lenhart et al. .................. 99/571
4,486,404 A * 12/1984 Weinert ........................... 424/54

FOREIGN PATENT DOCUMENTS

| CN | 101 007 991 A | 8/2007 |
| DE | 37 00 188 A1 | 7/1988 |
| EP | 1174145 A2 * | 1/2002 |
| JP | 62081325 A * | 4/1987 |
| JP | 2005-008571 A | 1/2005 |
| KR | 2002 054 014 A | 7/2002 |

OTHER PUBLICATIONS

O'Connor, J T. "Aesculus Hippocastanum" from: The American Homoeopathic Pharmacopoeia. Boericke & Tafel: New York, Philadelphia, Chicago, 1883. pp. 57-58.*

Henriette. "Making tinctures" from: On the medicinal herblist in (Sep. 2000) [Retrieved from the internet on: Oct. 24, 2011]. Retrieved from the Internet: <URL: http://www.henriettesherbal.com/articles/tincture.html>.*

International Search Report for PCT/JP2009/052602, mailed Jun. 22, 2009 from the European Patent Office, Rijswijk, the Netherlands.

International Preliminary Report on Patentability including the Written Opinion of the International Searching Authority for PCT/JP2009/052602, mailed Aug. 17, 2010 from the International Bureau of WIPO, Geneva, Switzerland.

World Patent Index (WPI) English language abstract for KR 20020054014, published Jul. 6, 2002 (listed as XP-002531197 on the International Search Report for PCT/JP2009/052602).

World Patent Index (WPI) English language abstract for CN 101007991, published Aug. 1, 2007 (listed as XP-002531198 on the International Search Report for PCT/JP2009/052602)).

Patent abstract of Japan, English language abstract for JP-A-2005-008571, published Jan. 13, 2005.

Fujimura, T. et al., "A horse chestnut extract, which induces contraction forces in fibroblasts, is a potent anti-aging ingredient," J Cosmet Sci 57(5): 369-376 (Sep. 2006), Society of Cosmetic Chemists.

"Communication pursuant to Article 94(3) EPC" for EP Appl. No. 09 709 818.0-2107, mailed Sep. 25, 2012, from the European Patent Office, Munich, Germany.

Čukanović, J. et al., "Biochemical composition of the horse chestnut seed (*Aesculus hippocastanum* L.)," Arch. Biol. Sci. Belgrade 63(2):345-351 (2011), Serbian Biological Society, Belgrade, Serbia.

* cited by examiner

*Primary Examiner* — Amy L Clark
(74) *Attorney, Agent, or Firm* — Sterne, Kessler, Goldstein & Fox P.L.L.C.

(57) ABSTRACT

To provide a method for producing a Hippocastanaceae plant seed extract which is less colored and is suitably incorporated into a composition such as a pharmaceutical product or a cosmetic composition. A method for producing a Hippocastanaceae plant seed extract, which includes removing hulls from seeds of a Hippocastanaceae plant, followed by extraction with a solvent.

13 Claims, 5 Drawing Sheets

METHOD FOR PRODUCING *HIPPOCASTANACEAE* PLANT SEED EXTRACT

TECHNICAL FIELD

The present invention relates to a method for producing an extract from seeds of a plant belonging to the family Hippocastanaceae.

BACKGROUND ART

In general, seeds of a plant belonging to the family Hippocastanaceae (hereinafter such a plant may be referred to as a "Hippocastanaceae plant"), such as *Aesculus Hippocastanum* (horse chestnut) or *Aesculus turbinata* are used as feed for sheep or pigs, or as a source of starch. As has been known, an extract of Hippocastanaceae plants or a triterpenoid saponin isolated from the extract (called escin) exhibits excellent anti-inflammatory and astringent effects. Therefore, for example, an extract from seeds of horse chestnut has been used as an anti-inflammatory drug in an oral, intramuscular injection, or external-use form for the post-surgical treatment or the treatment of post-traumatic swelling. Also, an extract from horse chestnut has been used as a raw material of cosmetic compositions. Recent studies have revealed that an extract from horse chestnut exhibits an effect of preventing or ameliorating skin wrinkles or sagging of the skin (Patent Document 1).

However, since seeds of Hippocastanaceae plant have dark brown hulls, when an extract is prepared through extraction of crushed seeds of the plant with a solvent, the extract poses problems in that it assumes a brown color and is easily discolored in a water-containing drug product.

Hitherto, there has been no finding that the site of a seed of the plant that contains an ingredient exhibiting an effect of preventing or ameliorating skin wrinkles or sagging of the skin.

Patent Document 1: JP-A-2005-8571

SUMMARY OF THE INVENTION

The present invention provides a method for producing an extract from seeds of a Hippocastanaceae plant (hereinafter the extract may be referred to as a "Hippocastanaceae plant seed extract"), comprising removing hulls from seeds of a Hippocastanaceae plant, followed by extraction with a solvent.

The present invention also provides a Hippocastanaceae plant seed extract produced through the aforementioned method.

DETAILED DESCRIPTION OF THE INVENTION

Figure 1:
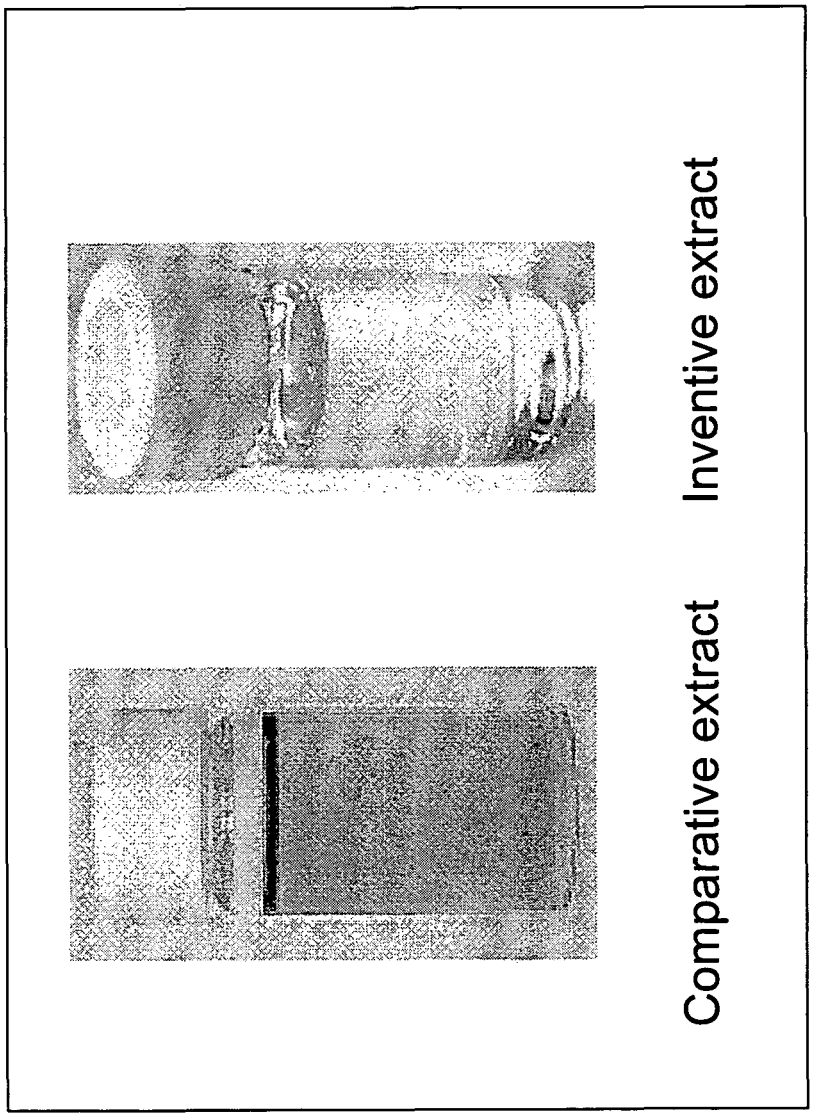
FIG. 1 shows the hues of an inventive extract and a comparative extract.

The present invention is directed to a method for producing a Hippocastanaceae plant seed extract which is less colored and is suitably incorporated into a composition (e.g., a pharmaceutical composition or a cosmetic composition).

The present invention has been accomplished on the basis of the finding that when a Hippocastanaceae plant seed extract is produced by removing hulls from seeds of a Hippocastanaceae plant, followed by extraction with a solvent, disadvantageous coloring of the extract is significantly suppressed without losing a useful active ingredient.

The production method of the present invention can produce a Hippocastanaceae plant seed extract which is less colored, without a losing useful active ingredient of the Hippocastanaceae plant seeds that exhibits an effect of preventing or ameliorating skin wrinkles or sagging of the skin. Thus, the Hippocastanaceae plant seed extract prepared through the production method of the present invention is useful as an ingredient of, for example, a cosmetic composition or a pharmaceutical product which effectively utilizes a pharmacological effect (e.g., an effect of preventing or ameliorating skin wrinkles or sagging of the skin) of the Hippocastanaceae plant seeds.

The method for producing a Hippocastanaceae plant seed extract of the present invention includes a step of removing hulls from seeds of a Hippocastanaceae plant, followed by extraction with a solvent.

The Hippocastanaceae plant employed in the present invention is preferably a plant belonging to the genus *Aesculus*. Examples of the Hippocastanaceae plant include *Aesculus turbinata*, *Aesculus hippocastanum* (horse chestnut), and *Aesculus chinensis* (Chinese horse chestnut), all of which belong to the family Hippocastanaceae. Of these, *Aesculus hippocastanum* (horse chestnut) is preferred.

No particular limitation is imposed on the method for removing hulls from seeds of a Hippocastanaceae plant. For example, the hulls may be peeled from the seeds through crushing of the seeds by means of powder machinery such as a grinder or a grinding granulator. Subsequently, the crushed seeds may be applied to a closed-circulation-type pneumatic separator, to thereby remove the hulls on the basis of the difference in weight between the hulls and the remaining parts of the seeds.

The seeds separated from the hulls (containing mainly endosperm) may be subjected to solvent extraction directly, or may be crushed before solvent extraction.

The extraction solvent may be a polar solvent, a nonpolar solvent, or a mixture thereof. Examples of the extraction solvent include water; alcohols such as methanol, ethanol, propanol, and butanol; polyhydric alcohols such as propylene glycol and butylene glycol; ketones such as acetone and methyl ethyl ketone; esters such as methyl acetate and ethyl acetate; acyclic and cyclic ethers such as tetrahydrofuran and diethyl ether; polyethers such as polyethylene glycol; halogenated hydrocarbons such as dichloromethane, chloroform, and carbon tetrachloride; hydrocarbons such as hexane, cyclohexane, and petroleum ether; aromatic hydrocarbons such as benzene and toluene; pyridine compounds; supercritical carbon dioxide; oil and fat; wax; and other oils. Of these, water, an alcohol, and a water-alcohol mixture are preferred. More preferably, aqueous ethanol (in particular, 20 to 80% (vol/vol) aqueous ethanol) is employed.

Extraction conditions may vary with the type of a solvent employed. For example, when the extraction solvent is water, an alcohol, or a water-alcohol mixture, preferably, extraction is carried out by using the solvent in an amount of 1 to 50 parts by volume on the basis of 1 part by mass of Hippocastanaceae plant seeds separated from the hulls at 4 to 100° C. (preferably 20 to 60° C.) for 1 hour to 30 days (more preferably 1 to 14 days, even more preferably 1 to 3 days).

The thus-produced extract is less colored and has reduced odor, and therefore the extract may be directly employed as the Hippocastanaceae plant seed extract of the present invention. Alternatively, the extract may be diluted, concentrated, or lyophilized and then optionally prepared in the form of powder or paste.

Inert contaminants may be removed from the extract through liquid-liquid partition or a similar technique. Optionally, the resultant extract may be further subjected to deodorization, decoloration or other treatments in accordance with a known technique.

The thus-prepared Hippocastanaceae plant seed extract is significantly less colored as compared with an extract prepared in the same manner from whole Hippocastanaceae plant seeds including hulls (see Test Example 2). Further, the thus-prepared Hippocastanaceae plant seed extract significantly increases contraction force generated by human skin fibroblasts, as compared with an extract prepared in the same manner from whole Hippocastanaceae plant seeds including hulls (see Test Examples 1 and 3). Contraction force generated by skin fibroblasts is attributed to formation of stress fibers which accompanies actin polymerization, and a substance which increases contraction force generated by skin fibroblasts is suggested to be effective for preventing aging of skin tissue, such as sagging of the skin, loss of skin elasticity or formation of wrinkles (J. Cosmet. Sci., 57, 369-376, 2006). Thus, the Hippocastanaceae plant seed extract prepared through the method of the present invention is useful as an ingredient of cosmetic compositions, pharmaceutical compositions or other compositions effectively utilizing a pharmacological effect of the extract (e.g., an effect of preventing or ameliorating skin wrinkles or sagging of the skin).

EXAMPLES

Example 1

Preparation of Hippocastanaceae Plant Seed Extract (1) Plant Employed
  i) *Aesculus hippocastanum* (horse chestnut) (from Poland)
  ii) *Aesculus chinensis* (from China)
  iii) *Aesculus turbinata* (from Japan)
(2) Preparation Method Seeds of each plant (10 kg) were crushed by means of a grinding granulator (product of Dalton Co., Ltd.) for five minutes, and the thus-crushed seeds were treated with a closed-circulation-type pneumatic separator (product of Nihon Senki) (wind energy: 200) for 20 minutes, to thereby separate the seeds into hulls peeled-off and crushed matter (containing mainly endosperm). Thus, a crushed product for extraction (8 kg) was prepared. 50 vol % Ethanol (1 L) was added to the crushed product (100 g), and the mixture was stirred at 50° C. for 24 hours for extraction, followed by filtration. 50 vol % Ethanol (1 L) was added to the residue, and extraction was carried out again. The thus-obtained extracts were combined, and solvent was removed through evaporation under reduced pressure, followed by preparing 50 vol % EtOH solutions (solid content: 1.0 w/v % and 0.5 w/v %). The solutions thus obtained were used as inventive extracts 1 to 3 in the following Test Examples.

Inventive extract 1: extract from hull-free seeds of *Aesculus hippocastanum*
Inventive extract 2: extract from hull-free seeds of *Aesculus chinensis*
Inventive extract 3: extract from hull-free seeds of *Aesculus turbinata*

For comparison, extracts were prepared as described below from seeds of each of the aforementioned Hippocastanaceae plants with hulls.

50 vol % Ethanol (1 L) was added to a crushed product (100 g) prepared from seeds of each plant, and the mixture was stirred at 50° C. for 24 hours for extraction, followed by filtration. 50 vol % Ethanol (1 L) was added to the residue, and extraction was carried out again. The thus-obtained extracts were combined, and the solvent was removed through evaporation under reduced pressure, followed by preparing 50 vol % EtOH solutions (solid content: 1.0 w/v % and 0.5 w/v %). The solutions thus obtained were used as comparative extracts 1 to 3 in the following Test Examples.

Comparative extract 1: extract of *Aesculus hippocastanum* seeds with hulls
Comparative extract 2: extract of *Aesculus chinensis* seeds with hulls
Comparative extract 3: extract of *Aesculus turbinata* seeds with hulls

Test Example 1

Determination of Hue

The hue (Gardner color scale) of each of inventive extracts 1 to 3 and comparative extracts 1 to 3 prepared in Example 1 (i.e., a 50 vol % EtOH solution (solid content: 1.0% or 0.5%)) was determined by means of a Gardner colorimeter in accordance with the method described in "JIS K0071-2, Testing method for color of chemical products, Part 2, Gardner color scale." The results are shown in Table 1. FIG. 1 shows the appearance of inventive extract 1 and comparative extract 1 (50 vol % EtOH solution (solid content: 1.0%)).

As shown in Table 1 and FIG. 1, in the inventive extracts, coloring was significantly suppressed, as compared with the comparative extracts. Also, the odor of the inventive extracts was improved.

TABLE 1

| | | Gardner color scale | | | |
| | | Solid content in Extract: 1.0 w/v % | | Solid content in Extract: 0.5 w/v % | |
| | | Inventive extract | Comparative extract | Inventive extract | Comparative extract |
| 1 | *Aesculus hippocastanum* | 3 | 6 | 1 | 4 |
| 2 | *Aesculus chinensis* | 4 | 6 | 3 | 5 |
| 3 | *Aesculus turbinata* | 4 | 6 | 2 | 5 |

Test Example 2

Measurement of Contraction Force Generated by Cells

Measurement of contraction force generated by cells was carried out in a collagen gel culture system in accordance with the method of Kolodney, et al. (Kolodney M S., Wysolmerski R B., Isometric contraction by fibroblasts and endothelial cells in tissue culture: a quantitative study. J. Cell Biol., 117, 73-82 (1992), Kolodney M S., Elson E L., Correlation of myosin light chain phosphorylation with isometric contraction of fibroblasts. J. Biol. Chem., 268, 23850-23855 (1993)). Human skin fibroblasts (Dainippon Pharmaceutical Co., Ltd., Osaka, Japan, passage number: 3 to 8) were employed. A fibroblasts-embedded collagen gel ($1.5 \times 10^6$ cells, 1.5 mg/mL collagen, Nitta Gelatin Type I-A) was suspended and immobilized in a beaker charged with about 70 mL of serum-free medium (Dulbecco's modified Eagle's medium (DMEM)) (medium temperature: 37° C.), and the collagen gel was stabilized for one hour under a tension of about 200 mg weight. Thereafter, inventive extract 1 or comparative extract 1 prepared in Example 1 (1.0 mL), which was diluted with a serum-free DMEM to about 70 times of its final concentration (final solid concentration: 0.00025 to 0.001%), was added to the collagen gel culture. Contraction force generated by human skin fibroblasts was measured by means of an isotonic transducer (8 gf, T-7-8-240, ORIENTEC, Japan) and recorded by means of BIOPAC system (BIOPAC Systems Inc., Santa Barbara, Calif., USA). The results are shown in Table 2.

TABLE 2

| Extract evaluated | Average (dyne) | SD |
| --- | --- | --- |
| Inventive extract 1 0.001% | 28 | 9.1 |
| Inventive extract 1 0.0005% | 22 | 7.5 |
| Inventive extract 1 0.00025% | 16.25 | 5.7 |
| Comparative extract 1 0.001% | 15.75 | 1.5 |

As shown in Table 2, in the case of inventive extract 1 (i.e., extract from hull-free seeds of *Aesculus hippocastanum*), contraction force generated by human skin fibroblasts was increased four times or more than that in the case of comparative extract 1 (i.e., extract of *Aesculus hippocastanum* seeds with hulls), in terms of the concentrations of the extracts at which contraction forces generated by human skin fibroblasts were comparable.

Example 2

Preparation of Extract Evaluated by Human

A crushed product from hull-free seeds of *Aesculus hippocastanum* was prepared in a manner similar to that described in Example 1. 75 vol % Ethanol (1 L) was added to the crushed product (100 g), and the mixture was heated at 50° C. for six hours under stirring for extraction. After cooling to room temperature, filtration was carried out, and 75 vol % Ethanol (1 L) was added to the residue. Extraction was carried out again under the same conditions as described above, followed by filtration. The resultant two extracts were combined, and 1,3-butylene glycol (240 g) was added to the mixture. The mixture was concentrated under reduced pressure, and the concentrate was allowed to stand still at a low temperature for one week, followed by filtration, to thereby remove insoluble matter. 1,3-Butylene glycol and water were added to the resultant product, to thereby prepare a 80% 1,3-butylene glycol solution (3.5 L) (solid content: 0.5 w/v %). Thus, inventive extract 4 was prepared.

The above procedure was repeated, except that the crushed product from hull-free seeds of *Aesculus hippocastanum* was replaced with a crushed product of *Aesculus hippocastanum* seeds with hulls, to thereby prepare comparative extract 4.

Test Example 3

Measurement of Contraction Force Generated by Cells

In a manner similar to that described in Test Example 2, contraction force generated by human skin fibroblasts was measured in the presence of inventive extract 4 or comparative extract 4 prepared in Example 2 (solid content: 0.5 w/v %) at a final solid concentration of 0.01%. The results are shown in Table 3.

TABLE 3

| Extract evaluated | Average (dyne) | SD |
| --- | --- | --- |
| Inventive extract 4 | 9.5 | 1.3 |
| Comparative extract 4 | 2.8 | 0.5 |

As shown in Table 3, the extract from hull-free seeds of *Aesculus hippocastanum* increased contraction force generated by human skin fibroblasts, even when the extract had been subjected to solid-liquid partition or a similar treatment after extraction.

Test Example 4

Test on Humans (1) Test Design

Double-blind comparative test was carried out on a half-face of seven healthy female subjects (age: 30s to 40s) having wrinkles at the outer corners of their eyes using a test sample containing inventive extract 4 prepared in Example 2 and a placebo sample not containing inventive extract 4. Each subject was applied a predetermined sample to areas around her eye every day (twice or thrice a day) for two months. Table 4 shows the formulations of samples tested.

TABLE 4

| Ingredients (mass %) | Test sample | Placebo sample |
| --- | --- | --- |
| Inventive extract 4 | 3.0 | — |
| Xanthan gum | 0.1 | 0.1 |
| 86% Glycerin | 5.0 | 5.0 |
| Methylpolysiloxane | 4.0 | 4.0 |
| Carboxyvinyl polymer | 0.4 | 0.4 |
| Potassium hydroxide | 0.6 | 0.6 |
| Cetyl dimethylbutyl ether | 0.1 | 0.1 |
| Neopentyl glycol dicaprate | 0.1 | 0.1 |
| 1,3-Butylene glycol | 3.0 | 3.0 |
| Polyethylene glycol | 3.0 | 3.0 |
| Succinic acid | 0.3 | 0.3 |
| Polyoxyethylene hydrogenated castor oil | 0.5 | 0.5 |
| Preservative | 0.3 | 0.3 |
| Perfume | Small amount | Small amount |
| 95% Synthetic alcohol | 0.5 | 0.5 |
| Purified water | Balance | Balance |

(2) Method for Evaluating Efficacy of Samples on Wrinkles (A) Scores Determined Through Visual Observation of Photographs Areas around the right and left eyes of each subject who was sitting and lightly closing the eyes were photographed with a digital camera (close-up photography) and then printed on 2 L-size sheets.

The samples were evaluated on the basis of the degree of wrinkles at the outer corners of the eyes observed in the photographs according to the following ratings: score 0: no wrinkles, score 1: a few wrinkles, score 2: some wrinkles, score 3: many wrinkles, and score 4: considerable wrinkles (in increments of 0.25 from score 1 to 5; i.e., a total of 17 levels). The score at the time of initiation of the two-month test was subtracted from the score at the time of termination of the test (test period: 2 months), and the samples were compared in terms of change in score.

(B) Analysis of Roughness on Replica

Figure 2:
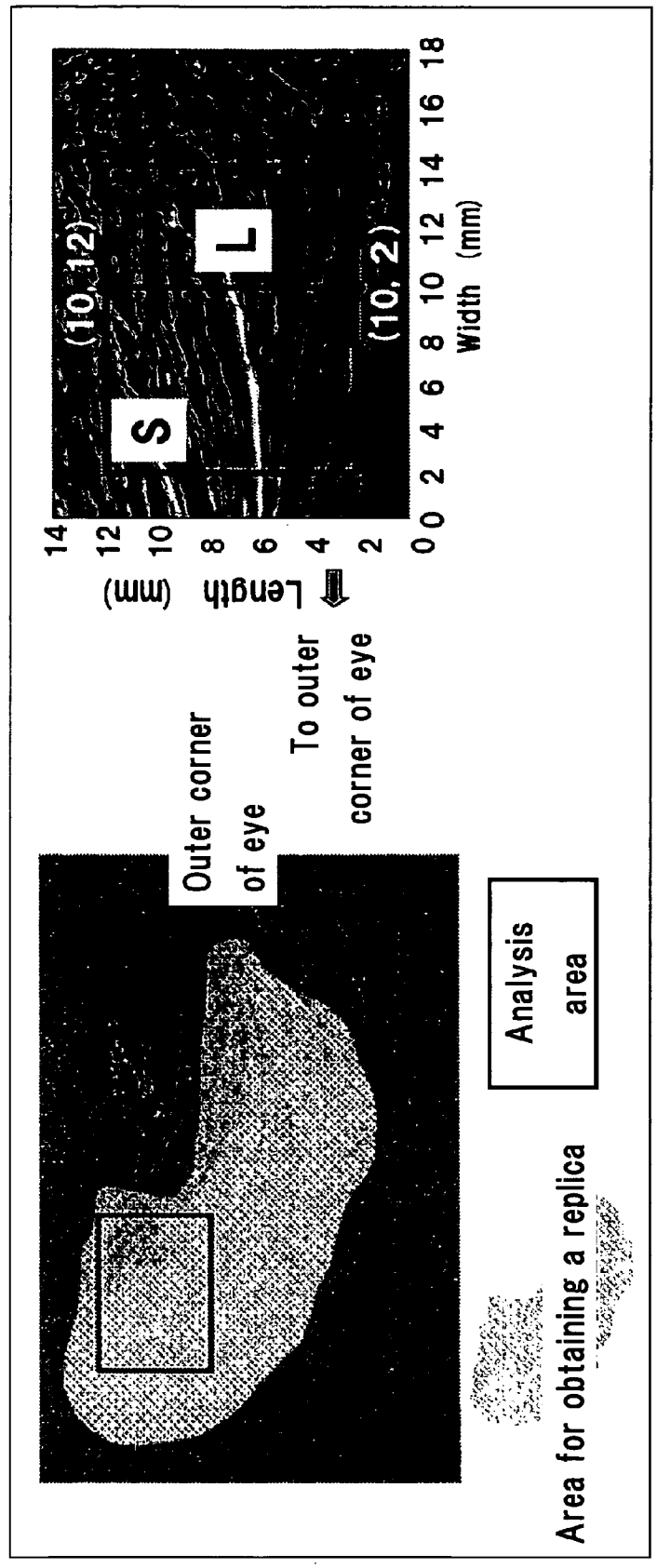
FIG. 2 shows the facial area from which a replica was obtained for line roughness analysis, and an analysis area of the replica (L: line located 10 mm away from the end on the side of the outer corner of the eye (L=10 mm), S: region of 2 mm to 14 mm away from the end on the side of the outer corner of the eye (area: 12 mm×10 mm)).

Replicas (Gc exafine, GC Co. Ltd., Tokyo, Japan) of areas around the right and left eyes were taken from each subject who was lying on her back and lightly closing the eyes. The thus-prepared replicas were subjected to three-dimensional roughness analysis using PRIMOS compact (GF Messetechnik GmbH, Berlin). FIG. 2 shows the facial area from which a replica was obtained, and an area employed for analysis.

By use of PRIMOS software (English version 4.0), configuration matching was carried out between a replica obtained at the time of initiation of the two-month test (reference) and a corresponding replica obtained at the time of termination of the test. As shown in FIG. 2, the site at which the configurations of the replicas were matched was designated as an area for roughness analysis of the outer corner of the eye. Line roughness and surface roughness in the area were determined by use of the software. The line roughness parameters employed were Ra (arithmetical mean roughness) and Rz (10-point mean roughness), and the surface roughness parameters employed were Sa (arithmetical mean height) and Sz (maximum height of scale limited surface).

(3) Results

Figure 3:
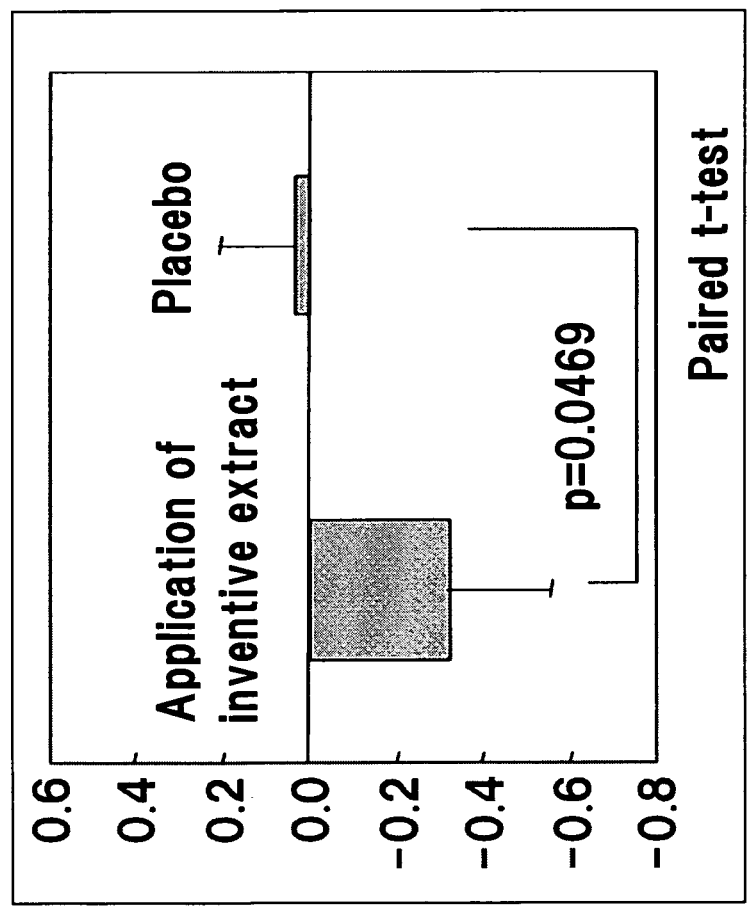
FIG. 3 shows change in score determined through visual observation of photographs of the outer corners of the eyes.

1) FIG. 3 shows change in score determined through visual observation of photographs of the outer corners of the eyes.

In the placebo group, no significant difference was observed between the score at the time of initiation of the two-month test and that at the time of termination of the test. In contrast, in the inventive extract 4 application group, a significant reduction in score was observed.

Figure 4:
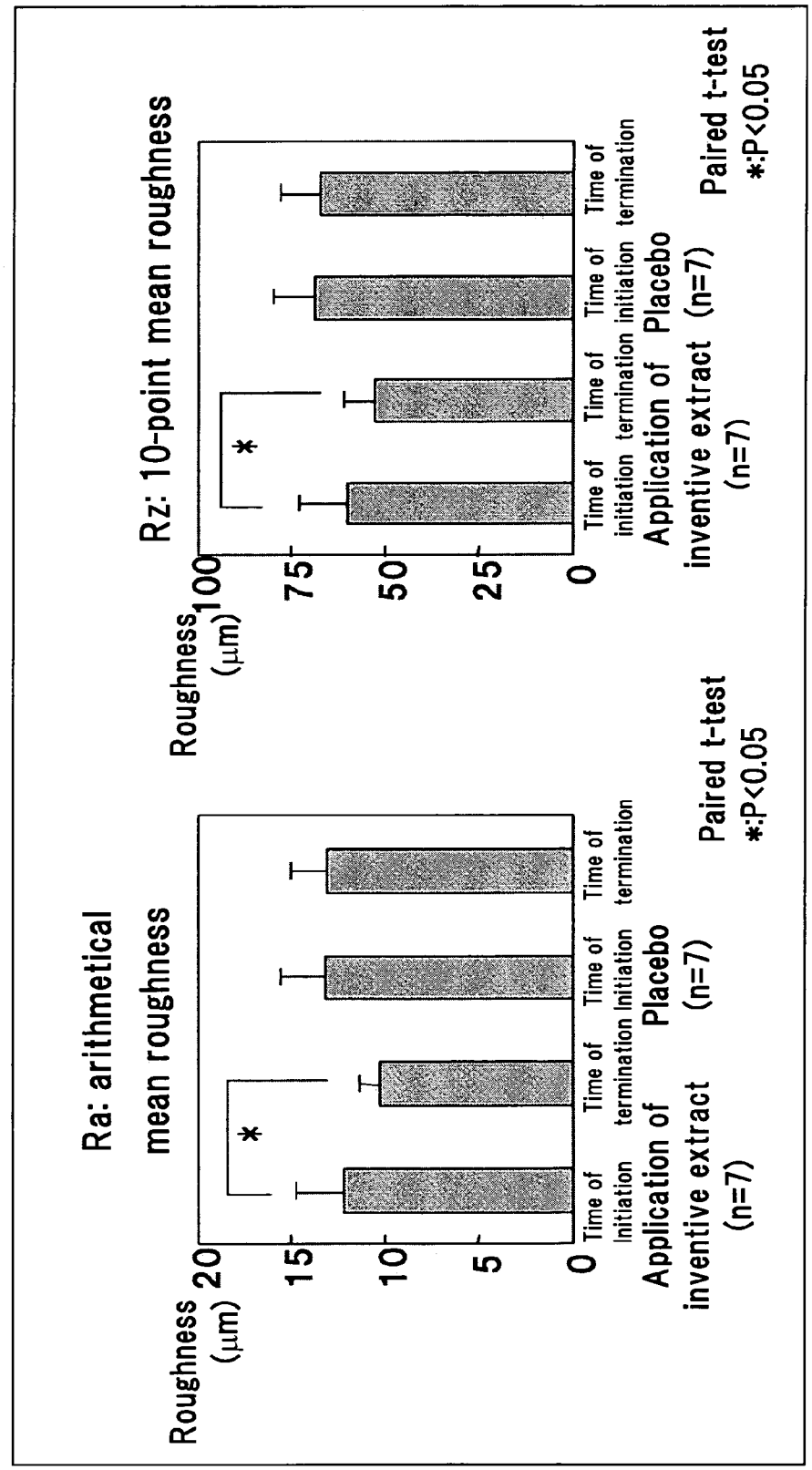
FIG. 4 shows data of Ra and Rz obtained through line roughness analysis of replicas.
Figure 5:
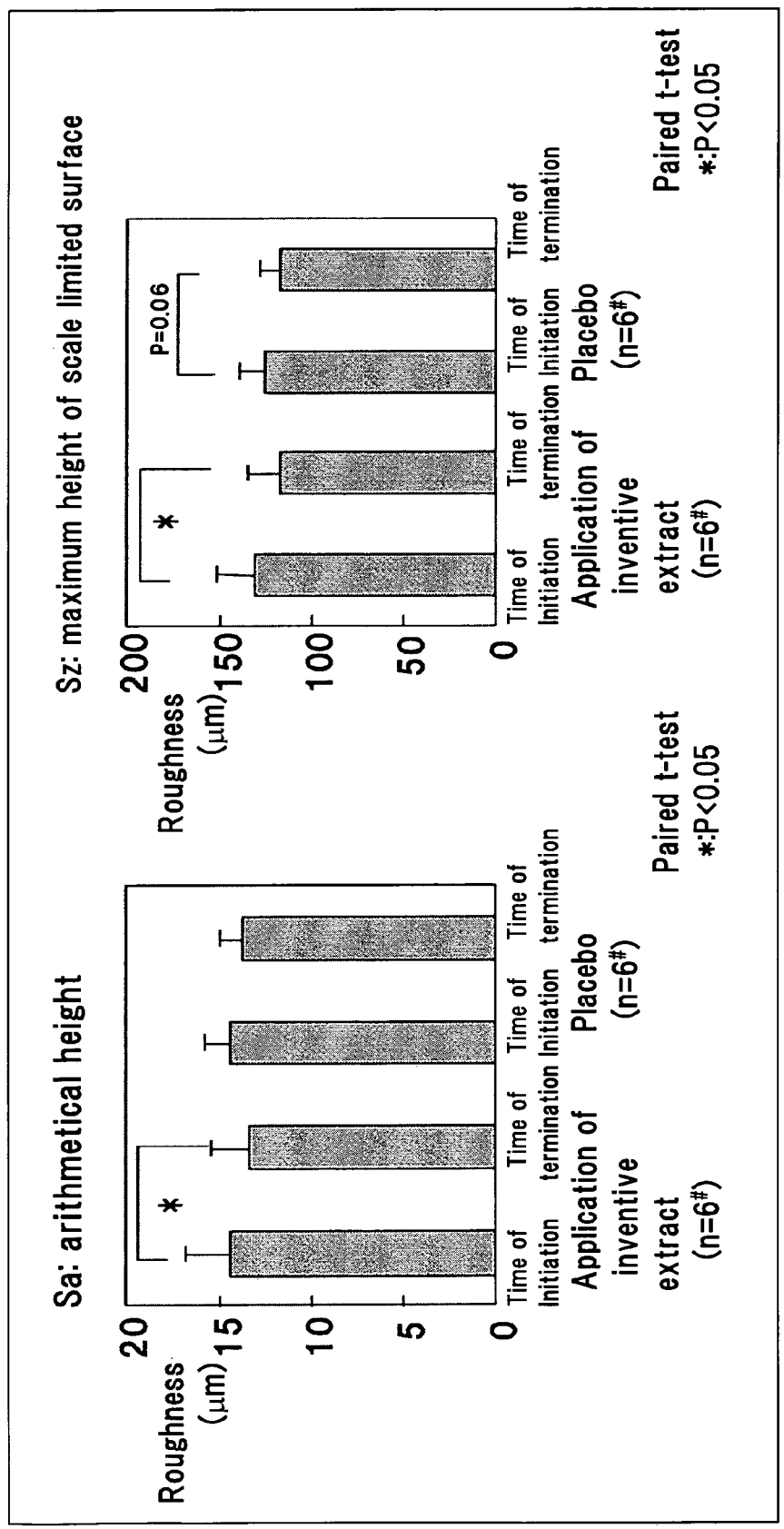
FIG. 5 shows data of Sa and Sz obtained through surface roughness analysis of replicas (#: analysis data of replicas from six subjects (n=6), exclusive of one in which air bubbles were included.

2) FIG. 4 shows data of Ra and Rz obtained through line roughness analysis of replicas. FIG. 5 shows data of Sa and Sz obtained through surface roughness analysis of replicas (FIG. 5 shows analysis data of six subjects exclusive of one subject, as the replica from the one subject has air bubbles in the area for analysis.

In the placebo group, line roughness analysis showed no significant difference between data at the time of initiation of the test and those at the time of termination of the test. In contrast, in the inventive extract 4 application group, a significant difference was observed between line roughness at the time of initiation of the test and that at the time of termination of the test; i.e., a significant reduction in Ra and Rz was observed.

Similar to the above case, surface roughness analysis in the placebo group showed no significant difference between data at the time of initiation of the test and those at the time of termination of the test. In contrast, in the inventive extract 4 application group, a significant reduction in Sa and Sz was observed.

The invention claimed is:

1. A method of making a Hippocastanaceae plant seed extract, comprising the steps of:
   i.) crushing seeds of a Hippocastanaceae plant prior to removing hulls from said seeds to provide crushed seeds;
   ii.) removing and separating hulls from the crushed seeds of said Hippocastanaceae plant by peeling hulls from the crushed seeds by applying the crushed seeds to pneumatic separation, wherein said hulls are removed and separated to provide hulls and a remaining part of crushed seeds, wherein said separation is by a difference in weight between the hulls and the remaining part of the crushed seeds; and
   iii.) extracting said remaining part of the crushed seeds with a solvent, to produce said Hippocastanaceae plant seed extract.

2. The method of claim 1, wherein the solvent in step iii.) is a water-alcohol mixture.

3. The method of claim 1 or 2, wherein the Hippocastanaceae plant is *Aesculus hippocastanum*.

4. The method of claim 1, wherein said extracting in step iii.) occurs at a temperature of 4° C. to 100° C.

5. The method of claim 1, wherein said extracting in step iii.) occurs at a temperature of 20° C. to 60° C.

6. The method of claim 1, wherein said extracting in step iii.) is carried out for 1 hour to 30 days.

7. The method of claim 1, wherein said extracting in step iii.) is carried out for 1 hour to 14 days.

8. The method of claim 4, wherein said extracting in step iii.) is carried out for 1 day to 3 days.

9. The method of claim 1, wherein said extracting in step iii.) is carried out twice to provide two extraction.

10. The method of claim 9, wherein the two extractions are carried out at 50° C. for 24 hours.

11. The method of claim 1, wherein said extracting of step iii.) comprises:
   extracting 1 part by mass of the remaining part of the crushed seeds with 1 to 50 parts by volume of water, alcohol, or a water-alcohol mixture, at 4° C. to 100° C. for 1 hour to 30 days to provide said Hippocastanaceae plant seed extract; and removing inert contaminants from said Hippocastanaceae plant seed extract.

12. The method of claim 1, wherein said extracting of step iii.) comprises:
   adding 50 vol % ethanol to the remaining part of the crushed seeds to create a mixture; stirring said mixture at 50° C. for 24 hours;
   filtering said misture to provide a residue and a first extract;
   re-extracting the residue to provide a second extract; and combining the first and second extracts; and
   removing remaining solvent.

13. The method of claim 1, wherein said extracting of step iii.) comprises:
   adding 75 vol % ethanol to the remaining part of the crushed seeds to create a mixture; stirring said mixture at 50° C. for 6 hours;
   cooling to room temperature, followed by filtrating said mixture to provide a residue and a first extract;
   re-extracting the residue to obtain a second extract, and combining the first and second extracts; and
   removing insoluble components from the combined extracts.

* * * * *